United States Patent [19]

Iamartino et al.

[11] Patent Number: 5,171,580
[45] Date of Patent: Dec. 15, 1992

[54] ORALLY-PHARMACEUTICAL PREPARATIONS WITH COLON SELECTIVE DELIVERY

[75] Inventors: Piero Iamartino, Monza; Grazia Maffione; Lino Pontello, both of Milan, all of Italy

[73] Assignee: Boehringer Ingelheim Italia S.p.A., Florence, Italy

[21] Appl. No.: 687,304

[22] Filed: Apr. 18, 1991

[30] Foreign Application Priority Data

Oct. 20, 1988 [IT] Italy ................. 22379 A/88

[51] Int. Cl.⁵ .............................. A61K 9/16
[52] U.S. Cl. ...................... 424/490; 424/471; 424/460; 424/461; 424/462
[58] Field of Search ............... 424/471, 461, 490, 460, 424/491, 462

[56] References Cited

U.S. PATENT DOCUMENTS 3,431,338 3/1969 Munzel et al. .............. 424/471
4,716,040 12/1987 Panoz ........................ 424/491
4,755,385 7/1988 Etienne et al. ............. 424/490

FOREIGN PATENT DOCUMENTS 0040590 11/1981 United Kingdom .
0225189 6/1987 United Kingdom .

*Primary Examiner*—Thurman K. Page
*Assistant Examiner*—William E. Benston
*Attorney, Agent, or Firm*—Robert A. Elwell; Harold D. Jastram

[57] ABSTRACT

Orally administrable pharmaceutical preparation containing an active ingredient to be released in the lower part of the gastrointestinal tract, i.e. in the large intestine, and especially colon, consisting of a core containing a therapeutically active substance and coated with three protection layers at different solubility. The manufacturing and the use of these preparations are also described.

16 Claims, No Drawings

ORALLY-PHARMACEUTICAL PREPARATIONS WITH COLON SELECTIVE DELIVERY

BACKGROUND OF THE INVENTION

The present invention relates to a novel orally administrable pharmaceutical preparation containing an active ingredient to be released in the lower part of the gastrointestinal tract, i.e. in the large intestine and especially in the colon.

There is an important and increasing need of a pharmaceutical delivery system which enables a selective release in the lower part of the gastrointestinal tract, i.e. in the large intestine and especially in the colon.

Such a delivery system would be of great benefit in the case of a therapy which requires the administration of a medicament in the large intestine. A first therapeutic application of such a system is for the treatment of colonic and rectal disorders. Orally administrable pharmaceutical preparations are frequently found to be ineffective in this respect as a result of the absorption or degradation of the pharmacologically active ingredient in the digestive tract before the colon or rectum is reached. Consequently, the delivery of pharmacologically active agents to the colon or rectum has conventionally been achieved by rectal administration, by the use of either suppositories or enemas. However, the spreading of these preparations within the large intestine is highly variable even in healthy subjects (Int. J. Pharm. 25, 191-197, 1985) and it often fails to reach the trasverse and ascending colon. In particularly, suppositories are only effective for the rectum and the sigmoid whereas enemas rarely reach the ascending colon. Furthermore, rectal administration generally is less convenient and less acceptable than oral administration. As a consequence, it is evident that orally administrable preparations with a colon selective release would be very effective and convenient for the treatment of large intestine and of rectal disorders.

Colon-localized release of the active ingredients is also desiderable in the treatment of infectious diseases of large intestine caused by microbial growth of pathogenic agents. In such a case, by using an orally administrable colon selective delivery system, a high in-situ concentration level of antibacterial agents can be attained and a more beneficial local effect with respect to common preparations can be ensured.

The need of a colon selective delivery system is also highly desirable for the administration of antitumour agents in the cancer therapy of large intestine. In fact, the release of antitumour agents specifically in this part of the gastrointestinal tract which is affected by the disease allows to reach locally an high effective drug concentration and, at the same time, to strongly reduce the side effects due to absorption in the small intestine.

An other therapeutic possibility of a colon selective delivery system is to administer drugs which are poorly absorbed in the small intestinal tract and to give significant therapeutic effect either locally or systemically when they reach the large intestine.

For instance in the treatment of irritable bowel syndrome some antispasmodic agents show a direct action on the smooth muscle. Therefore, by using a colon selective delivery system, such antispasmodic agents can produce their effects in their specific site of action avoiding any (even erratic) small intestinal absorption and obtaining a more selective effect on the large intestinal smooth muscle.

An other very important reason for the application of the colon selective delivery system is the possibility to administer orally drugs which are degraded by the gastroduodenal juices or which induce side effects in the stomach or small intestine.

Particularly, a colon selective delivery system can be successfully applied for the oral administration of proteins and peptides, of which the poor efficacy if orally administered, is well known owing to their degradation in gastric and duodenal juices.

It is also known that Peyer's patches which are present in the ileocecal junction can have a role in protein absorption through lymphatic uptake. As a consequence, the release of proteins and peptides in the lower part of the intestine can be a means to permit an oral administration of such compounds which for the above difficulties are normally administered through parenteral route. It is evident the great advantage resulting from this possibility is much more acceptable and convenient for patients than injection formulations.

In the last years many attempts have been made to obtain an oral pharmaceutical preparation which enables drugs to be released in the lower region of the intestine preferentially in the large intestine or colon.

From EP 40590 orally administrable pharmaceutical preparations consisting of coated granules whose coating comprises a mixture of an anionic carboxyacrylic polymer which is soluble only at pH 5.5 and a water insoluble polymer selected from quaternary ammonium substituted acrylic polymers are known. The disadvantage of this delivery system is that this release can occur even after only 1-2 hours at pH 7 because of the presence of a mixture of the two polymers, for which there is the possibility that part of the drug is released before reaching the colon. From WO 83/00435 a solid oral dosage form coated with a suitable amount of an anionic polymer (Eudragit ®S) soluble in aqueous medium only at pH 7 is known. The disadvantage of this formulation is due to the use of significant amount of Eudragit ®S so that the dosage form remains intact until it reaches the colon. In such a case there is the possibility that the preparation is eliminated before a complete dissolution of the coating takes place.

From EP 225189 a colon selective delivery system which consists of a soft gelatin capsule containing the drug (proteins and peptides) and coated with a film forming composition which is insoluble at pH below 7 is known. The coating composition consists of a mixture of suitable amounts of copolymer of methacrylic acid and of its ester (Eudragit ®S, L, S). Due to biological variability of pH in the gastro-intestinal tract, the reliability of this system is rather low and the relevant risks are the release before the colon due to an early pH above 7 or the elimination of the intact form without release in the colon.

From BE Pat. 903502 an osmotic system to release the drug in the colon is also known. In this case the release is based on the use of enteric coating polymers which dissolve in the intestine and prime the osmotic pump.

BE-A-652807 relates to an orally administrable preparation for gradual and sustained release in the colon consisting of:
(a) a core containing a therapeutically active susbtance
  (b) 1. an inner layer soluble at acidic pH and insoluble at basic pH 2. an intermediate layer water soluble at any pH (consisting or arabic gum, gelatin, page 11–12 Ex. in particular page 12, line 12)
3. an outer layer soluble at basic pH and insoluble at acidic pH.

SUMMARY OF THE INVENTION

We have now found, and this is the object of the present invention, that a core containing a therapeutically active substance with a coating of a particular composition allows a more specific and reliable release of the active substance directed to the lower part of the intestine especially to the large intestine (colon). The present invention thereof relates to a novel orally administrable pharmaceutical preparation containing a medicament to be released in the lower part of the gastrointestinal tract, especially in the large intestine or colon, consisting of a core containing a therapeutically active substance and of a coating characterized in that it comprises the following three layers:
1) an inner layer, comprising a suitable amount of an anionic copolymer which is soluble at pH above 7.0 and a suitable plasticizer;
2) an intermediate layer, comprising a suitable amount of a gelling polymer which swells in the enteric juice at any pH building up a thick gel layer;
3) an outer layer, comprising a suitable amount of a gastro-resistent polymer able to dissolve quikly in the intestine.

DETAILED DESCRIPTION OF THE PREFERRED EMBODIMENT

The core may contain the therapeutically active substance alone or in admixture with carrier materials or dispersed on the surface of a carrier particle.

Anionic polymers used as supports which dissolves at pH above 7, include polymers derived from methacrylic acid and methyl methacrylate. The ratio of free carboxyl group to the ester group is approximately 1:2. The mean molecular weight of the copolymer is approximately 135,000 Eudragit ®S. This copolymer is used in an amount of 10 to 30 percent by weight gain on the core. Preferably Eudragit ®S is used in an amount of 12 to 18 percent by weight gain on the core. The amount of Eudragit ®S has been determined in order to get a film thickness of about 40–120 microns preferably 60–80 microns, which ensures a quick dissolution of the coating layer at pH above 7.0.

Suitable plasticizers, present in an appropriate amount in order to make coating process possible and to obtain an even coating film, include polyethylene glycol, dibutylphthalate, diethylphthalate, triacetin, castor oil and citric acid esters. The amount of the inner layer is calculated in order to obtain a quick release of the active ingredient when constant pH above 7.0 is reached after exhausting of the medium layer.

The gelling polymers used in the intermediate coating layer are polymer materials which easily swell in aqueous media at any pH building up a thick gel layer. Useful gelling polymers include methyl cellulose, carboxymethylcellulose, hydroxypropylcellulose, hydroxypropylmethylcellulose, polyvinylalcohols, polyoxyethyleneglycols, polyvinylpyrrolidone or their mixture, preferably hydroxypropylmethylcellulose (Methocel ® K100, K4M and K15M) having a molecular weight of about 25,000 to about 120,000 and intrinsic viscosity of from about 100–15,000 mPa.s.

The gelling polymer is applied directly onto the first inner layer in an amount between 10 to 40 percent by weight, preferably 20–30 percent by weight gain on the core. The amount used corresponds to a coating thickness of about 40–120 um preferably 80–100 um, and allows to obtain a viscous gel layer when the preparation comes into contact with the enteric juice. The gelification process allows to obtain a delay in the dissolution of the pharmaceutical preparation.

The type and amount of the gel layer is chosedn as described above in order to obtain a delay of about 2–4 hours, because it has been proved that the transit time of a small size dosage unit through the small intestine is rather constant (S.T.P. Pharma 2 (22) 1015–1022, 1986) even in the presence of diarrhea or constipation. The combination of the gel layer with the pH sensitive inner layer ensures that during the intestinal transit time the enteric juice would not affect the inner layer even if a peak of pH above 7 should occur due to biological variability.

The gastroresistent polymer used in the outer layer is selected from the commonly used enteric materials such as cellulose acetate phthalate, hydroxypropylmethylcellulose phthalate, polyvinyl acetate phthalate, hydroxyethyl cellulose phthalate, cellulose acetate tetrahydrophthalate, preferably acrylic polymers such as the anionic copolymer derived from methacrylic acid and methylmethacrylate (Eudragit ® L) which dissolves at pH 5.5.

The therapeutically active substances which may be included in the embodiment of the present invention are those for which a beneficial effect can be obtained when they are released in the lower part of the intestinal tract preferably in the large intestine.

As active substances to be used in accordance with the present invention can be cited the following:
a) drugs used in the local treatment of colonic and rectal disorders e.g. colite ulcerosa of Crohn's morbus, such a 5-aminosalicylic acid or corticoids;
b) drugs used in the local treatment of infectious diseases of large intestine such as antibacterial agents and antibiotics;
c) drugs used in cancer therapy with localization in of the large intestine such as antitumour chemotherapeutic agents;
d) drugs which show a poor absorption in the upper part of the intestine or in the stomach and that can produce a beneficial therapeutic effect either locally or via systemic absorption when they are released in the lower part of the intestine. In this category antispasmodic drugs such as cimetropium bromide which have shown a local effect on the smooth muscle are included;
e) drugs which generally induce side effects in the stomach or small intestine, e.g. because of their irritating or ulcerating properties and for which absorption can occur in the lower part of the intestine with reduced side effects. In this category non steroidal antiinflammatory agents such as ketoprofen, ibuprofen and so on are included;
f) drugs which are degraded in the gastric or duodenal juices.

In this category are especially included peptide and protein drugs because of their favorable absorption when they are released in the lower intestinal tract., such as: insulin, gastrin, pentagastrin, calcitonin, glucagone, human growth hormone, adrenocorticotropic hormone, luteinizing hormone, enkephalin, oxytocin, parathyroid hormone, tyrotropic releasing hormone and vasopressin.

The process for the manufacturing of the pharmaceutical preparations, as above defined, consists in coating the cores, prepared according to known procedures with a three layer coating by spraying the respective coating solutions or dispersions in suitable solvents.

According to a practical procedure the cores containing the active principles may be prepared by a granulation or by tableting. In the first case their size may correspond with sieve fractions between 0.5 and 1.5 mm, whereas in tableting process the tablets diameter is of 2 mm. The cores so obtained may include pharmaceutical inert materials of the type normally used in pharmaceutical preparations such as polysaccharides, microcrystalline cellulose and waxes. On these cores the coating inner layer is applied by spraying by conventional methods an organic solution of the selected polymer (Eudragit ® S) together with an appropriate plasticizer. The intermediated layer is applied on the inner layer by spraying s suitable solution or dispersion of the gelling polymers employing a suitable mixture of solvents. For this purpose a mixture of a suitable solvent such as alcohol is preferably employed. The outer layer is then applied by spraying a suitable solution of the gastro-resistent polymer.

The tablets or the cores coated according to the invention are to be included in dosage units, for which each dosage unit normally contains at least about 10 coated cores. The number of coated cores depends obviously on the effective dose of the active substance which is used. Among suitable dosage units hard gelatine capsule may be mentioned. In the dosage units pharmaceutically acceptable additives may also be included.

The present invention will be now illustrated on the ground of some examples, which are not to be considered, however, as limitative:

EXAMPLE 1

The cores containing the pharmaceutically active substance were prepared according the following formulation:

| Ketoprofen | 2 mg |
| Lactose | 4.96 mg |
| Starch | 0.80 mg |
| Polyvinylpyrrolidone (PVP) | 0.16 mg |
| Magnesium stearate | 0.80 mg |

Ketoprofen, lactose and starch were mixed for 10 minutes in a planetary mixer. An aqueous solution of PVP was added slowly to the powder mixture to obtain an homogeneous granulate. The wet mass was sieved and dried in an drier at 50° C. for 16 h. The dried granules were calibrated through an appropriate screen and lubricated by adding magnesium stearate. Tablets of 2 mm diameter and weighting 8 mg each were manufactured by using a tablet press. The cores showed a disintegration time of about 2 minutes in water determined according to U.S.P. requirements. The cores were then submitted to the layer coating process as follows. The inner layer was applied onto the cores, previously heated at 45° C. in a rotary pan by continuous spraying at room temperature of the following solution:

| Eudragit S 100 | 8% w/w |

| -continued | |
|---|---|
| Diethylphthalate | 2% w/w |
| Ethanol 70% | 90% w/w |

The weight gain on the core was 1.2 mg of dried substance corresponding to a thickness of about 60 microns.

The intermediate layer was applied onto the so coated cores, heated at 45° C. in the same rotary pan by continuous spraying at room temperature of the following solution:

| Hydroxypropylmethylcellulose (Methocel K4M) | 4% w/w |
|---|---|
| Polyethyleneglycol 400 (PEG 400) | 0,5% w/w |
| Ethanol 95% | 85,5% w/w |
| Water | 10.0% w/w | prepared by adding slowly Methocel K4M to Ethanol 95% w/w under stirring and then adding to the Methocel alcoholic suspension so obtained an aqueous solution of PEG 400 at room temperature. Subsequently the cores were kept at a temperature above 35° C. The weight gain on the cores was 2 mg of dried substance corresponding to a thickness of about 100 microns.

The outer layer was applied onto the so doubly coated cores and heated at 45° C. in the same rotary pan by continuous spraying at room temperature of the following suspension:

| Eudragit L 100 | 8% w/w |
|---|---|
| Diethylphthalate | 2% w/w |
| Ethanol 80% | 90% w/w |

The weight gain on the cores was 0.6 mg of dried substance corresponding to a thickness of about 30 microns. The final coated cores showed an average weight of 11.8 mg.

25 coated cores were put into one hard gelatin capsule in order to obtain a dosage unit containing 50 mg of Ketoprofen.

In-vitro test

The rate of release of Ketoprofen was firstly determined by the paddle method, as described in USP XXI page 1244, at 37° C. and 50 rpm in a pH 7.4 phosphate buffer solution. From the solution samples were taken at different times and the amount of Ketoprofen released was determined spectrophotometrically.

The results of the release test are the following:

| Dissolution time of Ketoprofen at pH 7.4 in function of the released amounts expressed in percent | | | |
|---|---|---|---|
| | t 10% | t 50% | t 100% |
| Core, uncoated | 1' | 15' | 60' |
| Core, coated with the inner layer | 60' | 75' | 120' |
| Core, coated with the inner and the intermediate layer | 160' | 180' | 300' |
| Core, coated with the three layers | 170' | 180' | 300' |

Besides, the release tate of Ketoprofen was determined by the half-change method according Munzel, J. Pharm. Sci. 56, 773 (1967) and Arch. Pharm. 293, 766 (1960). Samples of solute were taken at different times and the amount of Ketoprofen released was determined spectrophotometrically.

The results of the release test are the following:

| pH | Time | percent of release |
|---|---|---|
| 1.2 | 1 h | 0 |
| 2.0 | 2 h | 0 |
| 6.4 | 3 h | 0 |
| 7.0 | 4 h | 0 |
| 7.2 | 5 h | 0 |
| 7.3 | 6 h | 5% |
| 7.4 | 7 h | 46% |
| 7.4 | 7.5 h | 77% |
| 7.4 | 8 h | 96% |

The results confirm that according to present invention a preparation giving the desired release properties is obtainable.

EXAMPLE 2

As an other model substance with different solubility characteristics was used Cimetropium bromide of the following preparation:

| | |
|---|---|
| Cimetropium bromide | 2 mg |
| Lactose | 4,96 mg |
| Starch | 0,80 mg |
| PVP | 0,16 mg |
| Magnesium stearate | 0,08 mg |

The manufacturing procedure of the cores was the same as described in Example 1

Each core, obtained by tableting, had a weight of 8 mg, a diameter of 2 mm and a disintegration time of 1 minute in water, determined according to the requirements of U.S.P. XXI. The cores were then coated with a three layer coating by applying the same solutions and working conditions as described in example 1. The final coated cores showed an average weight of 1.8 mg.

In-vitro test

The release rate of Cimetropium bromide was determined by the paddle method according to U.S.P. XXI page 1246, at 37° C. and 50 rpm in a pH 7.4 phosphate buffer solution. Samples of solution were taken at different times and the amount of Cimetropium bromide released was determined by HPLC.

| Dissolution time of cimetropium bromide in function of the released amounts expressed in percent | | | |
|---|---|---|---|
| | t 10% | t 50% | t 100% |
| cores, uncoated | 1' | 10' | 15' |
| cores coated with the inner layer | 5' | 20' | 100' |
| cores coated with the inner and the intermediate layers | 110' | 130' | 220' |
| cores. coated with the three layers | 120' | 160' | 240' |

Example 3

In-vivo experiment

As another model substance Toluidine Blue of the following preparation was used:

| | |
|---|---|
| Toluidine Blue | 2 mg |
| Lactose | 4.96 mg |
| Starch | 0.80 mg |
| PVP | 0.16 mg |
| Magnesium stearate | 0.08 mg |

The manufacturing procedure of the cores was the same as described in example 1. Each core, obtained by tableting, had a weight of 8 mg, a diameter of 2 mm and a disintegration time of 3 minutes in water, determined according to the requirements of U.S.P. XXI. The cores were coated with a three layers coating by applying the same solutions and working conditions as described in example 1. The final coated cores showed an average weight of 11.8 mg.

The tablets were inserted directly in the duodenum and the experiment was focused on the behaviour of the transport and disgregation of the tablets taking as an index of disgregation the consistency of coating and the position of staining in the gastrointestinal tract.

Animals (male CD-COBS rats, 200–225 g body weight, fasted for 24 hours, with free access to water) were lightly anaesthetized with ether and their abdomen was opened; three small tablets (11.8 mg) were inserted in the duodenum through a small incision performed in the upper part of the duodenum. The wound was sutured with metal claws.

The rats were killed at the following times (hours): 5, 10, 12, 18, 24, 32.

At each time three rats were employed.

At the end of the experiment the whole gut was excised, and its length measured before having it opened in order to explore both eventual stained spots and position and consistency of the tablets.

Results 5 h: tablets migrated for 75% of the whole lenght of the small bowel; the coating was not corroded and the color was not released.

10 h: tablets migrated for the entire lenght of the small bowel and reached to caecum; they started to disgregate and to release color 12 h: tablets were present in the caecum and colon, which were stained with different intensities of color 18 h: same picture as observed at the 12th hour 24h: tablets were completely disgregated; color and residue of coating were found in the caecum, colon and feces 32 h: tablets were expelled with the feces and color was observed again in the caecum, colon and feces.

Comments

In the duodenum, the tablets covered the whole length of the small bowel within 10 hours, without significant changes of the coating and no color release; in all cases no color was present in the small bowel but only in the caecum and colon, when the tablets started to disgregate.

The results confirm that by the process according to the present invention a preparation giving the desired release properties is obtainable.

Although the present invention has been described with reference to the preferred embodiments, workers skilled in the art will recognize the changes may be made in form and detail without departing from the spirit and scope of the invention.

We claim:

1. A pharmaceutical preparation, suitable for oral administration within a capsule, the preparation consisting of a core comprising a therapeutically active substance and a coating upon the core, the coating comprising:

an inner layer of plasticized anionic acrylic copolymer having a mean molecular weight of 135,000 and being soluble in aqueous media at a pH above 7.0;

an intermediate layer of a gel-forming modified cellulose polymer having a mean molecular weight between 25,000 and 120,000 and an intrinsic viscosity of from 100 to 15,000 mPa.s; and an outer layer of a gastroresistant polymer soluble in aqueous media at a pH above 5.5.

2. The preparation according to claim 1, characterized in that the anionic copolymer of said inner layer is a copolymer of methacrylic acid and methylmethacrylate, said anionic copolymer of said inner layer is present in an amount equal to from about 10 to about 30 percent of the weight of the core and said plasticized anionic acrylic copolymer of said inner layer further includes a plasticizer selected from the group consisting of polyethylene glycol, dibutylphthalate, diethylphthalate, triacetin, castor oil and citric esters.

3. The preparation according to claim 1, characterized in that said gelling polymer of said intermediate layer is present in an amount equal to from about 10 to about 40 percent of the weight of the core coated with the inner layer and is selected from the group consisting of methylcellulose, carboxymethylcellulose, hydroxypropylcellulose, and hydroxypropylmethylcellulose.

4. The preparation according to claim 3, characterized in that said gelling polymer is hydrixypropylmethylcellulose having a molecular weight of 25,000 to 120,000 and an intrinsic viscosity from 100 to 15,00 Pa.s, when a solution consisting of two percent by weight of the hydroxypropylmethylcellulose polymer in water is measured at 20° C.

5. The preparation according to claim 3, characterized in that the amount of said gelling polymer is included between 10 and 40 percent of the weight core.

6. The preparation according to claim 1, characterized in that said gastroresistant polymer of said outer layer is selected from the group consisting of hydroxypropylmethylcellulose phthalate, polyvinyl acetate phthalate, hydroxyethylcellulose phthalate, cellulose acetate tetrahydrophthalate, cellulose acetate tetrahydrophthalate, and copolymer of methacrylic acid and methylmethacrylate.

7. The preparation according to claim 1, characterized in that said therapeutically active substance is selected from the group consisting of 5-aminosalicylic acid, corticoids, antibacterial agents, antibiotics, antipasmodic agents, antiinflammatory drugs, peptides, proteins, antitumor and chemotherapeutic agents.

8. A pharmaceutical preparation consisting of a core comprising cimetropium bromide and a coating on the core characterized in that the coating comprises:

an inner layer of plasticized anionic acrylic copolymer having a mean molecular weight of 135,000 and being soluble in aqueous media at a pH above 7.0;

an intermediate layer of a gel-forming modified cellulose polymer having a mean molecular weight between 25,000 and 120,000 and an intrinsic viscosity of from 100 to 15,000 mPa.s; and an outer layer of a gastroresistant polymer soluble in aqueous media at a pH above 5.5.

9. A pharmacuetical preparation consisting of a core comprising ketoprofen, and a coating on the core characterized in that coating comprises:

an inner layer of plasticized anionic acrylic copolymer having a mean molecular weight of 135,000 and being soluble in aqueous media at a pH above 7.0;

an intermediate layer of a gel-forming modified cellulose polymer having a mean molecular weight between 25,000 and 120,000 and an intrinsic viscosity of from 100 to 15,000 mPa.s; and an outer layer of a gastroresistant polymer soluble in aqueous media at a pH above 5.5.

10. A process for manufacturing an orally administrable pharmaceutical preparation comprising a therapeutically active core and three coating layers having different solubilities and disintegrating properties, comprising the steps of:

providing a core;

spray-coating a first coating layer on said core by spraying a solution comprising an anionic copolymer which is soluble at a pH above 7.0, and a plasticizer;

spary-coating a gelling polymer forming a second, intermediate layer which easily swells in the enteric juice at any pH;

spray-coating a gastro-resistant polymer forming a third, outer layer which is insoluble in the gastric juice but soluble at a pH above 5.5; and wherein all of said spray-coating steps are carried out at room temperature.

11. The process of claim 10, characterized in that all of said organic solutions are hydro-ethanolic solutions.

12. The process of claim 10, characterized in that said gelling polymer of said second, intermediate layer is selected from the group consisting of methylcellulose, carboxymethylcellulose, hydroxypropylcellulose, hydroxypropylmethylcellulose, polyvinylalcohols, polyoxyethylene glycols, polyvinylpyrrolidone.

13. The process of claim 12, characterized in that said gelling polymer is hydroxypropylmethylcellulose having a molecular weight of 25,000 to 120,000 and an intrinsic viscosity from 100 to 15,000 Pa.s. measured in a 2% aqueous solution at 20° C.

14. The process of claim 10, characterized in that said anionic copolymer of said first layer is a copolymer of methylacrylic acid and methylmethacrylate, which copolymer is plasticized by a plasticizer selected from the group consisting of polyethylene glycol, dibutylphthalate, diethylphtalate, triacetin, castor oil and citric esters.

15. The process of claim 10, characterized in that said gastroresistant polymer of said outer layer is selected from the group consisting of hydroxypropylmethylcellulose phthalate, polyvinyl acetate phthalate, hydroxyethylcellulose phthalate, cellulose acetate tetrahydrophthalate, cellulose acetate phthalate and copolymer of methacrylic acid and methylmethacrylate.

16. The preparation according to claim 4, characterized in that the amount of said gelling polymer is included between 10 and 40 percent of the weight core.

* * * * *